(12) United States Patent
Parmar et al.

(10) Patent No.: US 12,708,536 B2
(45) Date of Patent: Aug. 18, 2026

(54) DEVICE AND METHOD OF RADIALLY COLLAPSING MEDICAL DEVICES

(71) Applicant: MERIL LIFE SCIENCES PVT LTD., Vapi (IN)

(72) Inventors: Harshad Amrutlal Parmar, Vapi (IN); Chirag Vinodbhai Patel, Valsad (IN)

(73) Assignee: MERIL LIFE SCIENCES PVT LTD., Vapi (IN)

( * ) Notice: Subject to any disclaimer, the term of this patent is extended or adjusted under 35 U.S.C. 154(b) by 102 days.

(21) Appl. No.: 18/011,693

(22) PCT Filed: Jun. 28, 2022

(86) PCT No.: PCT/IN2022/050592
§ 371 (c)(1),
(2) Date: Dec. 20, 2022

(87) PCT Pub. No.: WO2023/084532
PCT Pub. Date: May 19, 2023

(65) Prior Publication Data

US 2024/0115407 A1 Apr. 11, 2024

(30) Foreign Application Priority Data

Nov. 12, 2021 (IN) ............................ 202121051873

(51) Int. Cl.
*A61F 2/95* (2013.01)
*A61F 2/24* (2006.01)
(Continued)

(52) U.S. Cl.
CPC .......... *A61F 2/9524* (2020.05); *A61F 2/2427* (2013.01); *A61F 2/95* (2013.01);
(Continued)

(58) Field of Classification Search
CPC ........ A61F 2/2433; A61F 2/95; A61F 2/9522; A61F 2/2524; A61F 2002/958;
(Continued)

(56) References Cited

U.S. PATENT DOCUMENTS 8,215,149 B1 7/2012 Kokish et al.
2024/0148528 A1* 5/2024 Wang .................... A61F 2/2427

FOREIGN PATENT DOCUMENTS

WO 2013016549 1/2013

OTHER PUBLICATIONS

PCT Application No. PCT/IN2022/050592, International Search Report, Oct. 10, 2022.

* cited by examiner

*Primary Examiner* — Brian D Keller
*Assistant Examiner* — Aaron R McConell
(74) *Attorney, Agent, or Firm* — KNH LLP

(57) ABSTRACT

A device and method of radially collapsing a medical device is disclosed. The device is in the form of an improved crimper which is capable of crimping a medical device. The crimper includes without limitation one or more of, a base plate, a stopper, two side plates, two housing plates with a handle, a plurality of jaws, two guide plates, at least one gear ring and a plurality of gear pins. The jaws, when assembled, collectively form an iris opening. The assembly of the crimper has a central opening through which the iris opening can be accessed. The device to be crimped is introduced in the central opening and held within the iris opening. The crimping is achieved by reducing the size of the iris opening (by moving the jaws simultaneously with respect to each other in synchronized manner) which in turn reduces the diameter of the prosthetic device.

36 Claims, 10 Drawing Sheets

(51) Int. Cl.
*B21D 39/04* (2006.01)
*B30B 7/04* (2006.01)
*B21J 9/06* (2006.01)

(52) U.S. Cl.
CPC .............. *B21D 39/048* (2013.01); *B30B 7/04* (2013.01); *B21J 9/06* (2013.01); *Y10T 29/49925* (2015.01); *Y10T 29/49927* (2015.01)

(58) Field of Classification Search
CPC ............ A61F 2002/9583; B65D 45/32; B65D 45/325; Y10T 29/53996; Y10T 29/53987; Y10T 29/49925; B25B 27/10; B25B 13/14; B25B 13/16; B25B 13/44; H01R 43/0424; H01R 43/058; H01R 43/0585; B21D 39/046
USPC .................................. 29/282, 283.5; 72/402
See application file for complete search history.

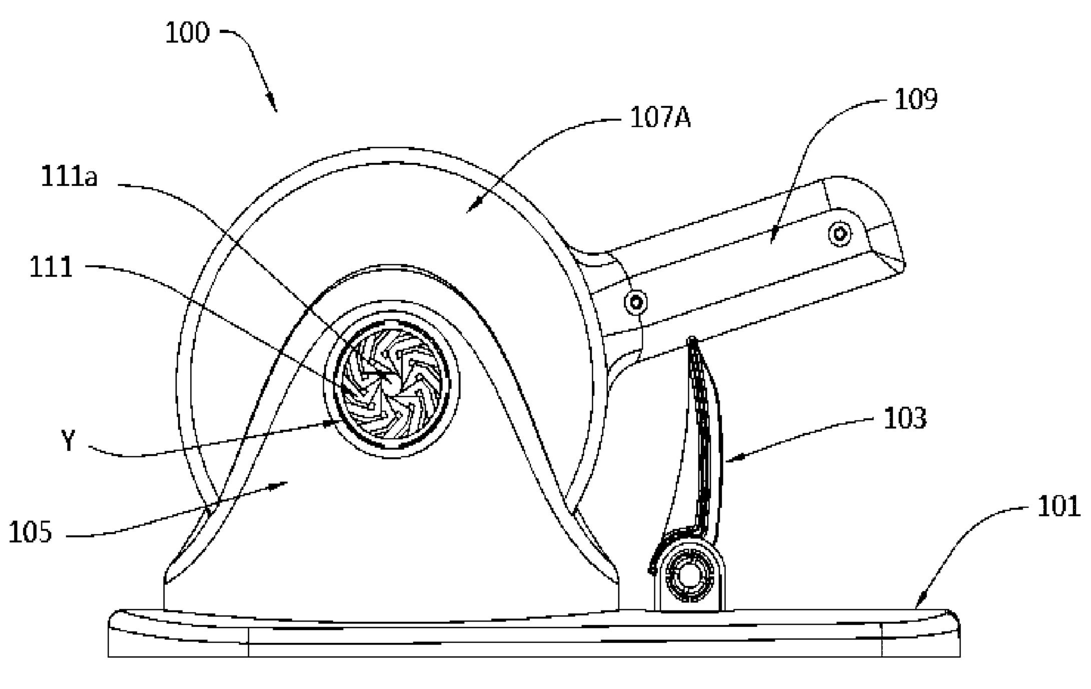
Fig 1
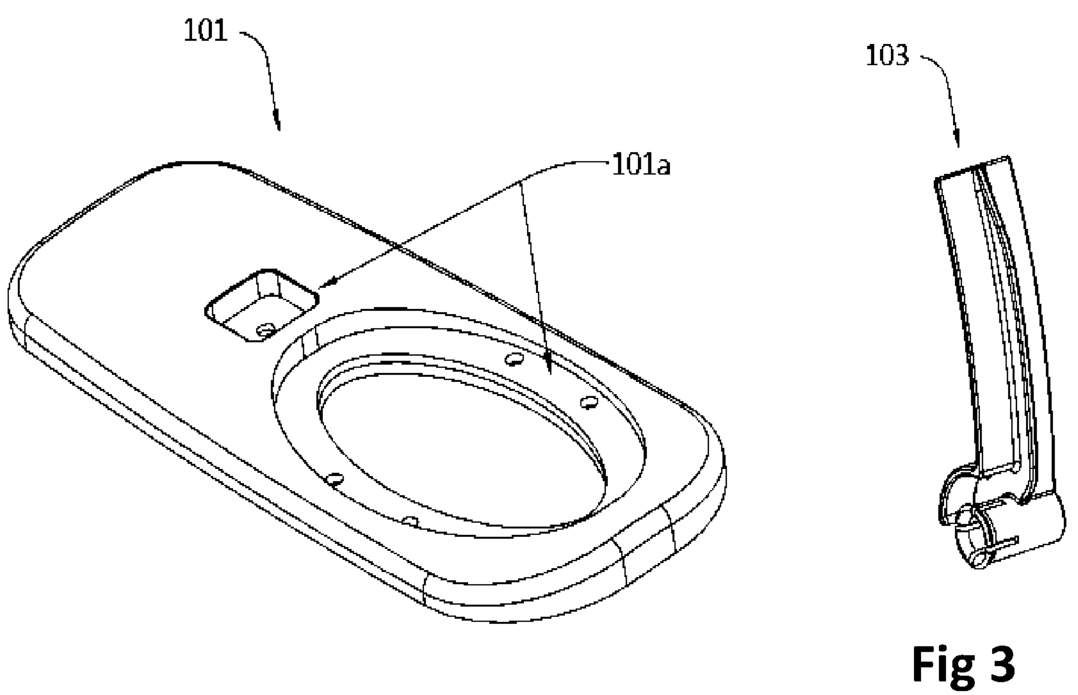
Fig 2
Fig 3

DEVICE AND METHOD OF RADIALLY COLLAPSING MEDICAL DEVICES

FIELD OF INVENTION

The present invention relates to an apparatus and a method of radially collapsing a prosthetic device that has a support structure i.e. a frame which is radially collapsible and expandable such as a stent/scaffold. Specifically, the invention relates to reducing diameter of trans-catheter prosthetic heart valves (THV) including a support structure (stent/scaffold/frame) and leaflets made of biological tissue material or a synthetic material which are radially collapsible.

BACKGROUND

Generally, prosthetic devices that are targeted for implantation within a lumen of a body vessel include a support structure or a frame that is radially collapsible and expandable. The support structure/frame of the prosthetic device is cylindrical in shape and may include a uniform diameter or a tapered shape or may include varying diameter across its axial length. Such a prosthetic device is implanted by introducing it into a lumen of a body vessel by a known catheterization technique which includes radially collapsing (also referred to as 'crimping') the prosthetic device on the delivery catheter. It is known to a skilled person that crimping of a prosthetic device is necessary to make it possible to reduce the entry profile and thus introduce it into and advance it through a patient's vasculature to the implantation site where the prosthetic device is implanted by radially expanding the frame. The frames of these devices may be self-expanding or balloon expandable. Balloon-expandable prosthetic devices are generally crimped from an initial large diameter to a reduced diameter on the balloon of a balloon catheter. The prosthetic device is radially expanded at the implantation site by expanding the balloon by pressurizing it with a fluid, generally saline. A skilled person is familiar with structure and functioning of a balloon catheter.

The prosthetic device, crimped on the balloon of a delivery balloon catheter, must be firmly secured onto the balloon. If the device is loose on the balloon, it may change its position on the balloon and even may get dislodged from the balloon during its introduction into and subsequent maneuvering through the patient's vasculature. Prosthetic devices that are not properly secured to the balloon may slip/dislodge and either be lost or potentially get embolized. In addition, crimping should be done in such a way as to minimize or prevent distortion of the prosthetic device and damage to the components of the prosthetic device. At the same time, the crimping process should not cause any damage to the balloon which may lead to leakage of blood into the balloon or leakage of inflation fluid out from the balloon. Such damage may weaken the balloon causing its bursting.

The process of crimping includes positioning the prosthetic device (also referred to as 'prosthesis') with at least partially expanded diameter over the collapsed or partially expanded balloon of the balloon catheter and then crimping the prosthesis over the balloon using a crimping device, also referred to as a 'crimper'.

Classically, crimpers are provided with movable elements referred to as "jaws" which have inclined surfaces. The jaws when assembled, collectively form an aperture (also referred to as an opening) similar to an iris aperture of a camera. This opening has a depth enough to at least partially accommodate a prosthesis that is at least partially in a radially expanded form. The shape of the opening is a uniform polygon which may be described as nearly circular. These jaws move in a synchronous manner to reduce or increase the size/diameter of the aperture. The crimper includes a mechanism for such movement of the jaws.

As mentioned above, the iris opening formed by the inclined surfaces of the jaws is a regular polygon with nearly circular shape. It is obvious to a skilled person that increasing the number of jaws will result in more number of sides of the polygon formed by them. The shape of the opening formed by more number of jaws will form a smoother circle than less number of jaws. This is because the length of sides of the polygon will be shorter as the number of jaws increases. The crimpers available in market generally incorporate twelve jaws which are found adequate and optimal.

It is advisable that the minimum size of the iris opening may be controlled so as to avoid over-crimping which may cause possible damage to the frame structure and also to the soft elements within the device such as soft biological tissue, polymeric components etc.

Traditionally, the replacement of a defective heart valve of a patient has been carried out by open heart surgery which has a higher risk as the patients requiring heart valve replacement are of old age, generally more than 70 years with concomitant comorbidities. Many patients are not clinically fit enough to undergo such surgery and hence cannot be treated. In recent years, trans-catheter prosthetic heart valves (THV) have become more popular as this technique does not require open heart surgery and hence the risk is reduced considerably.

The diameter of a THV in an expanded condition is typically in the range of about 19 to 32 mm. The scaffold structure (frame/stent) of a THV holds the valve structure made of leaflets of a biological material such as pericardium. The THV is normally stored in a preserving liquid (generally a dilute solution of glutaraldehyde) in the expanded or partially expanded configuration. THV with dry leaflets is being developed but has not yet commercialized. Alternatively, the valve component may be made of synthetic materials such as polyurethane (PU) or any other such material known in art and stored dry. When the THV is stored in a liquid, it is crimped on the balloon of a balloon catheter (delivery system) just before implantation procedure. The THV with dry leaflets may be pre-crimped over the balloon of a delivery catheter. In either situation, the stent frame/scaffold containing the valve component will need to be crimped over the balloon of the delivery system.

Although the crimpers for THV perform adequately, a need exists for a crimper that moves the jaws uniformly to apply uniform pressure on a THV with a large diameter (up to 32 mm) and reduce it to 6 mm or less without inducing high mechanical stresses within the crimper and also to the THV. The operation of the crimper should be simple and the cost of its manufacturing should be low.

SUMMARY OF INVENTION

The present invention describes an improved crimper and method for crimping stents/scaffolds or balloon expandable prosthetic devices such as THVs having a support frame. Though the invention describes apparatus and method of crimping with respect to THV, it is also suited for crimping other balloon expandable devices like vascular stents, stent grafts, etc.

The crimper of the present invention includes without limitation one or more of, a base plate, a stopper, two side plates, two housing plates with a handle, a plurality of jaws, two guide plates, at least one gear ring and a plurality of gear pins. Many of the components (viz. side plates, housing plates, guide plates) are in two parts i.e. two halves. Each part is either identical to the other part or a mirror image of the other part. These components are in two parts (or two halves) for ease of assembling the crimper as will be clear from the detailed description. For example, two parts (two halves) of housing plates, when assembled, form the "housing" with a handle. Similarly, two parts (two halves) of guide plates, when assembled, form a "guide housing".

The jaws, when assembled in a synchronous manner, collectively form an iris opening. The size of the iris opening can be reduced or increased by moving the jaws simultaneously with respect to each other in synchronized manner. The jaws can be moved in this manner by the mechanism described below. The assembly of the crimper has a central opening through which the iris opening can be accessed. The prosthetic device to be crimped is introduced in the central opening and held within the iris opening. The crimping is achieved by reducing the size of the iris opening which in turn reduces the diameter of the prosthetic device.

The movement of the handle imparts rotational movement to the entire assembly of the crimper. The movement of the handle up or down rotates the housing (assembly of two housing plates) and the gear ring(s) fixed inside the respective housing plate(s). The rotational movement of the gear ring(s) rotates the threaded heads of the gear pins which are engaged to the threads of the gear ring(s). The bottom pin portion of the gear pins have threads that are engaged to the threaded holes in the jaws. The rotation of the gear pins causes the movement of the jaws due to rotation of the threaded pin portion of the gear pins by engaging with more or less threads inside the holes in the jaws. The jaws are located within the guide housing (assembly of two guide plates) which have linear guides in the form of rails. The jaws have grooves which are engaged to the linear guides. Hence, the jaws move linearly by sliding along the linear guides of the guide plate in radial direction in a synchronized manner. Therefore, the movement of the jaws is entirely based on gears and threads on the gear pins and inside the threaded holes in the jaws. This results into smoother movement of the components and uniform crimping operation.

The upward movement of the handle increases the size of the iris opening and the downward movement reduces the size of the iris opening by moving the jaws in synchronized manner. A stopper may be removably attached onto the base plate to restrict the position of the handle when it is moved downward by not allowing the handle to move further down, thereby fixing the minimum size of the iris opening and restricting it from reducing further, thereby achieving a pre-determined crimped diameter. This pre-determined diameter may be an intermediate diameter or a diameter to prevent over-crimping of the medical device being crimped. Over-crimping may cause damage to the scaffold structure of a prosthetic device or to the soft biological tissue/synthetic material housed inside a THV. In an embodiment, there are more than one stopper to achieve different sizes of iris opening by replacing one stopper with another based on requirements of the crimping operation. In another embodiment, for a very low crimped diameter, the stopper is not used, allowing the handle to move further down to reduce the size of the iris opening further.

The method of crimping using the crimper of the present invention involves placing a medical device in at least partially expanded condition onto a deflated balloon of the delivery system. If desired, the balloon may be partially inflated so that the medical device can be fitted better onto the balloon. The handle of the crimper is then moved in an upward direction to increase the size of the iris opening more than the diameter of the prosthetic device. The balloon and the prosthetic device are introduced at least partially into the iris opening of the crimper. The handle is then moved in the downward direction to reduce the size of the iris opening. This downward movement is controlled manually so as to achieve reduction in the size of the opening in a gradual manner. This downward movement of the handle may also be automated using known automation techniques. The downward movement of the handle is stopped when desired crimping is achieved which may be in more than one stage. At this stage, the handle is moved upwards to increase the diameter of the opening enabling removal of the medical device crimped on the balloon from the crimper. If the balloon is partially inflated before crimping the prosthetic device, it should be gradually deflated during crimping operation.

Subsequently, the diameter of the crimped medical device is checked. If further crimping is required to reduce the crimped diameter further, the crimping operation is repeated and the handle is moved further down compared to the previous position.

BRIEF DESCRIPTION OF DRAWINGS

The summary above, as well as the following detailed description of illustrative embodiments, is better understood when read in conjunction with the appended figures. For the purpose of illustrating the present disclosure, various exemplary embodiments are shown in the figures. However, the disclosure is not limited to the description and figures disclosed herein. Moreover, those familiar with the art will understand that the figures are not to scale. Wherever possible, like elements have been indicated by identical numbers.

FIG. 1 depicts a crimper 100 in assembled condition showing the components which are visible externally in accordance with an embodiment of the present disclosure.

FIG. 2 depicts a base plate 101 of the crimper 100 in accordance with an embodiment of the present disclosure.

FIG. 3 illustrates a stopper 103 of the crimper 100 in accordance with an embodiment of the present disclosure.

DETAILED DESCRIPTION

Figure 4:
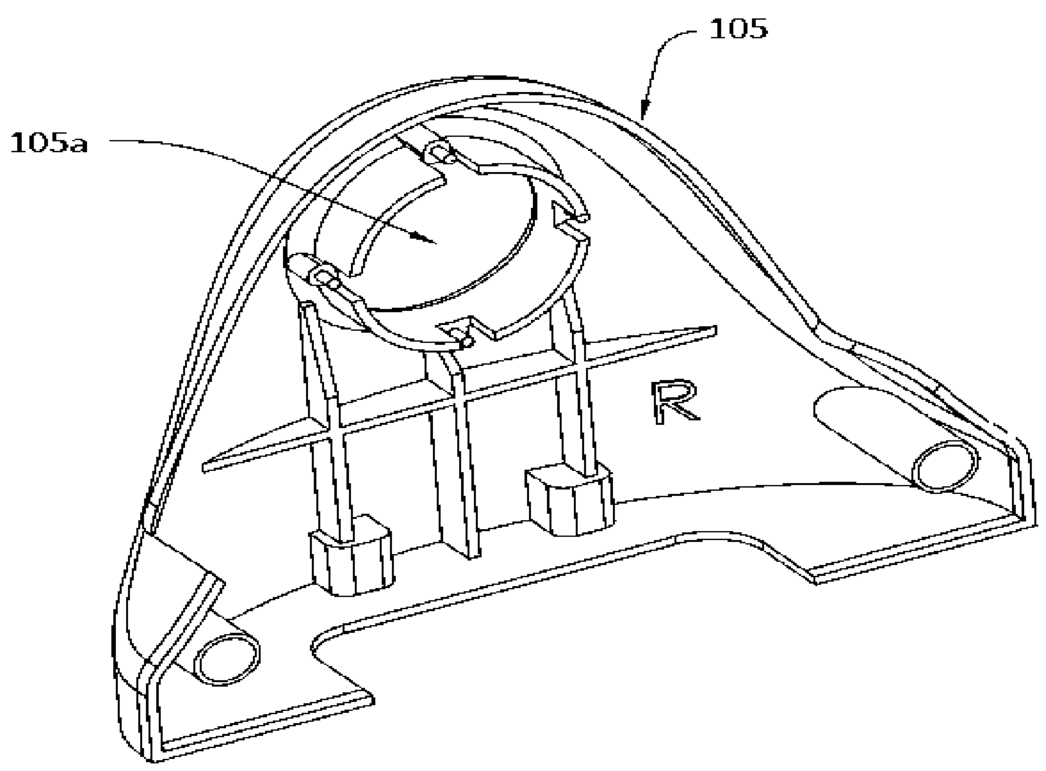
FIG. 4 depicts a side plate 105 of the crimper 100 in accordance with an embodiment of the present disclosure.

Prior to describing the invention in detail, definitions of certain words or phrases used throughout this patent document will be defined: the terms "include" and "comprise", as well as derivatives thereof, mean inclusion without limitation; the term "or" is inclusive, meaning and/or; the phrases "coupled with" and "associated therewith", as well as derivatives thereof, may mean to include, be included within, interconnect with, contain, be contained within, connect to or with, couple to or with, be communicable with, cooperate with, interleave, juxtapose, be proximate to, be bound to or with, have a property of, or the like; Definitions of certain words and phrases are provided throughout this patent document, and those of ordinary skill in the art will understand that such definitions apply in many, if not most, instances to prior as well as future uses of such defined words and phrases.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Although the operations of exemplary embodiments of the disclosed device/apparatus or method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed herein. Moreover, for the sake of simplicity, the attached figures may not show the various ways in which the disclosed system, method, and apparatus can be used in combination with other systems, methods, and apparatuses.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments. These features and advantages of the embodiments will become more fully apparent from the following description and apportioned claims, or may be learned by the practice of embodiments as set forth hereinafter.

The present invention discloses an apparatus and method of radially collapsing medical devices/prosthetic devices that have support structures i.e. frames which are radially collapsible and expandable such as stents/scaffolds/support frames which are balloon expandable or self-expandable. The medical device/prosthetic device may include a prosthetic heart valve, say a trans-catheter heart valve (THV) having a support structure (stent/scaffold/frame) and leaflets made of biological tissue material or a synthetic material which are radially collapsible and seated within the support structure. In addition, the THV may include other components like one or more of an internal skirt, an external skirt, etc. These devices are generally balloon expandable.

Though the invention describes an apparatus and method of radially collapsing with respect to THV, it is also suited for crimping other balloon expandable devices like vascular stents, stent grafts etc. The apparatus of the present invention is also suitable to crimp large size balloon expandable stents or prosthetic heart valves (THV) having expanded diameters as large as 32 mm or even more.

It should be noted that in the figures and the description to follow, the term 'prosthetic device' as used in the specification refers to balloon expandable prosthetic devices such as vascular stents, grafts or prosthetic valves for implanting into human vasculature, such as prosthetic heart valves (THV), venous valves and other similar valves. The term 'prosthetic valve' is also used for THV, venous valve or other similar valves.

The prosthetic heart valve includes a balloon expandable frame which supports a valvular structure attached to it by methods known in the art. As known in the art, the valvular structure may be made from a tissue such as pericardium e.g. bovine, porcine or equine pericardium. Alternatively, the valvular structure may be made from a synthetic material such as polyurethane (PU) or any other such material known in the art. The valvular structure may be attached to the frame by techniques known in the art, for example, suturing. The prosthetic heart valve may have other components like internal skirt, external skirt, commissure support fabrics, etc. The internal and external skirts may be made from a tissue or fabric such as polyethylene terephalate (PET).

Likewise, the terms 'delivery system', 'delivery catheter', or 'catheter' refer to the delivery apparatus used for implanting prosthetic devices in a human vasculature. These terms are used interchangeably but carry the same meaning.

Further, the apparatus of the present invention may be used to crimp self-expanding stents or prosthetic valves which can be loaded in a crimped condition into a restraining sheath instead of crimping them on a balloon.

The apparatus used for reducing the diameter of such medical devices is referred to as a "crimping device", "crimper" or "crimping apparatus" in the following specification. The process of reducing the diameter of the medical device is referred to as "crimping" in the following specification. In the case of a balloon expandable prosthetic device, the so called crimping results into mounting the medical/prosthetic device on a deflated balloon of a delivery catheter by radially compressing it on the balloon.

The crimper disclosed in this invention is capable of crimping a radially expandable and collapsible medical/prosthetic device in a single-stage or multi-stage crimping operation.

Now referring to figures, FIG. 1 depicts the externally visible components of the crimper 100 of the present invention. As mentioned above, the crimper 100 of the present invention is capable of crimping an expandable medical device (or expandable prosthetic device) for reducing the diameter of an expandable medical device from an at least partially expanded state to at least a partially crimped state.

The externally visible components of the crimper 100 as shown in FIG. 1 include a base plate 101, one or more stoppers 103 (optional), two side plates 105 and 105' (only one side plate 105 is visible as 105' is on the other side of the assembly), a housing 107A formed by assembling two housing plates 107 and 107', a handle 109 and a plurality of jaws 111 which form an iris opening 111*a* (also referred to as 'aperture 111*a*' or 'central opening 111*a*'). The crimper 100 also includes internal components that are internally placed within the externally visible components such as without limitation, one or more of, guide plates, gear rings, gear pins, etc. (discussed in detail below).

The components of the crimper 100 may be made of a biocompatible polymeric or reinforced polymeric materials where the reinforcement may be achieved by incorporating fibrous materials like glass fibre in the polymeric material. The polymeric materials may include acrylonitrile-butadiene-styrene (ABS), polyoxymethylene (POM), Nylon, polyester, polyamide polyether ether ketone (PEEK) etc. Alternately, the components of the crimper 100 may be made from biocompatible metals or metal alloys such as stainless steel, titanium etc. The components should have adequate mechanical strength. Alternately, the components of the crimper 100 may be made from a combination of polymeric and metallic materials. In a preferred embodiment of the crimper 100, the components are made from polymeric and reinforced polymeric materials such as ABS, polyamide and POM.

The assembled crimper 100 is placed on the base plate 101. The details of the base plate 101 is shown in FIG. 2. The base plate 101 may include a pre-defined shape such as circular, square, rectangular, oval etc. In an embodiment of FIG. 2, the pre-defined shape is rectangular. The shape of the base plate 101 is so selected that the surface area of the base plate 101 is good enough to firmly mount the assembled crimper 100 with adequate support and stability.

The exemplary base plate 101 of FIG. 2 includes a plurality of holes and cavities 101*a* to facilitate fixation of assembled crimper 100. The holes and cavities 101*a* shown in FIG. 2 are exemplary. The structure and dimensions of the holes and cavities 101*a* may correspond to the components of the assembly crimper 100 that mate with the base plate 101.

The optional one or more stoppers 103 may be adjustable and removable. Hence, the stopper 103 may be detachably (removably) attached to the base plate 101. The function of the stopper 103 is to restrict the downward movement of the handle 109 defining a lowermost position of the handle 109 to prevent the size of the iris opening 111*a* from reducing further. The length of the stopper 103 may depend on the specific requirement of a crimped diameter of the medical device being crimped. For example, smaller the length of the stopper 103, smaller is the crimped diameter of the medical device. There may be multiple stoppers 103 of different lengths, one of which may be attached to the base plate 101 to achieve specific crimped diameter. This arrangement facilitates crimping in multiple stages. FIG. 3 shows an exemplary stopper 103 of the present invention.

The crimper 100 of the present invention includes several components which are in two parts (two halves). These parts are either identical or mirror images of each other. For convenience, one of the part of these components is shown in the figures.

The present invention may further include at least two side plates. The embodiment of the crimper 100 described herein includes two side plates i.e. a first side plate 105 and a second side plate 105', one of which—the first side plate 105—is shown in FIG. 4. The function of the first and second side plates 105 and 105' is to support the housing 107A of the crimper 100 (described below) along with the other components housed inside the housing 107A. The side plates 105 and 105' may be structurally similar or different. In an embodiment, the crimper 100 includes two side plates 105 and 105' fixed on the base plate 101 such that the housing 107A is accommodated between them. In an embodiment, the first side plate 105 is a mirror image of the second side plate 105'.

The second side plate 105' is not shown as it is a mirror image of the first side plate 105. The exemplary first side plate 105 is in the form of a triangular plate having a predefined depth and required reinforcement strips to enhance mechanical strength. In the present embodiment, as shown in FIG. 4, each of the side plates 105/105' includes a central opening 105*a* which holds the assembled housing 107A with internal components (described below).

FIG. 1 shows the central opening 105*a* in the side plate 105 which is concentric with a central round opening in the housing 107A when assembled. The assembled housing 107A is held between the first and second side plates 105 and 105' such that the housing 107A is free to rotate around the central opening 105*a* of the side plates 105, 105'. As the first and second side plates 105 and 105' are fixed onto the base plate 101, the assembled housing 107A is adequately supported between the two side plates 105, 105'. A skilled person would appreciate that there are various ways of structuring the side plates 105/105' to support the assembled housing 107A between them.

The exemplary structure of the side plates 105/105' helps to hold and support the housing 107A of the crimper 100. However, it should be noted that the side plates 105/105' may include any other shape or structure and such structures are also within the scope of the present invention.

In an embodiment, the crimper 100 includes two housing plates 107 and 107', i.e. a right housing plate and a left housing plate held between the two side plates 105/105' which are fixed over the base plate 101 such that the housing plates 107, 107' are free to rotate relative to the base plate 101. Both the housing plates 107/107' of the present invention are mirror images of each other. When assembled, the two housing plates 107, 107' form the housing 107A.

Figure 5:
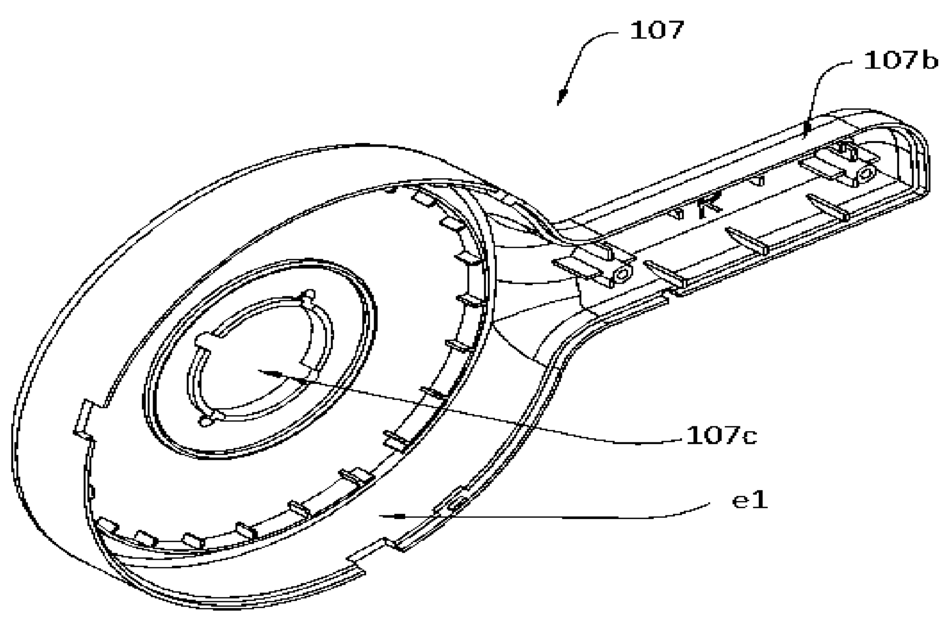
FIG. 5 shows a housing plate 107 of the crimper 100 in accordance with an embodiment of the present disclosure.

The structure of an exemplary embodiment of one of the housing plates 107 of the present invention is shown in FIG. 5. The other housing plate 107' is not shown as it is a mirror image of the housing plate 107. Each of the housing plates 107/107' are for example, circular in shape, with an internal diameter and a raised edge e1. The raised edge e1 may be for example, circular in shape. The raised edge e1 gives the housing plates 107/107' a shape which resembles a tray (for example, a circular tray portion) with an extended handle portion 107*b* integrally attached to the raised edge e1. The extended handle portion 107*b* of both the housing plates 107 and 107' when assembled, form the handle 109 of the housing 107A.

Each of the housing plates 107/107' may include a central housing opening 107*c* (or opening 107*c*). The central housing opening 107*c* as shown in FIG. 5, preferentially, has a circular (or round) shape.

The housing 107A formed by assembly of two housing plates 107 and 107' at the tray portions of each forms a housing and is utilized to accommodate/house the internal components of the crimper 100 (described below). The internal components of the crimper 100 are housed within the empty space of the housing 107A formed by joining/assembling the two housing plates 107/107' (described below in detail).

As shown in FIG. 1, the crimper 100 may include a plurality of jaws 111. In a preferred embodiment, the crimper 100 of the present invention includes twelve jaws 111. However, the number of jaws 111 may be less than or more than twelve. The jaws 111 move radially in a synchronized manner such that they collectively form the aperture 111*a* (or an iris opening) as shown in FIG. 1. The aperture 111*a* is an iris opening which is in the form of a regular polygon forming nearly a circular shape defining a size/diameter. The size/diameter of the aperture 111*a* can be varied in a controlled manner by movement of the jaws 111 in a synchronous manner on movement of the handle 109.

As mentioned above, the iris opening 111*a* is formed by a regular polygon. The number of sides of the polygon is same as the number of jaws 111. More the number of jaws 111, more are the sides of the regular polygon that form the iris opening 111*a* having a smoother opening tending to circular shape. In an embodiment, the iris opening 111*a* is formed by twelve jaws 111.

Figure 6:
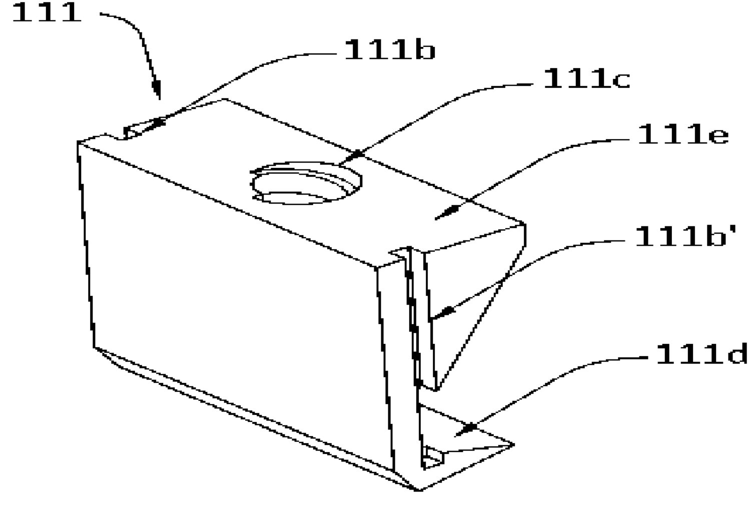
FIG. 6 shows a jaw 111 of the crimper 100 in accordance with an embodiment of the present disclosure.

It should be noted that the structure of all the jaws 111 is same/identical. However, other alternatives having jaws 111 with different structures are also within the scope of the present invention. FIG. 6 shows a single exemplary jaw 111. As shown in FIG. 6, each of the jaws 111 may include a set of grooves 111*b* and 111*b*', one on each of its two sides. The linear guides 113*a* of the guide plates 113/113' (described below) fit into the grooves 111*b*/111*b*'. In an embodiment, each of the grooves 111*b*/111*b*' has a width that corresponds to the width of the linear guides 113*a* of guide plates 113/113' such that the linear guides 113*a* can fit inside the grooves 111*b*/111*b*' in such a way that the jaws 111 can slide smoothly over the linear guides 113*a*.

The jaws 111 may further include a top surface 111*e* having a hole 111*c* with internal threads. As illustrated in FIG. 6, the top surface 111*e* is a flat surface. The said threads enable mating of the threads on a pin portion of the gear pin 117 (described below). Each jaw 111 has a tapered surface 111*d* at the end opposite to the top surface 111*e*. The tapered surfaces 111*d* of all the jaws 111 collectively form the iris opening 111*a* when all the jaws 111 are assembled within the guiding plates 113/113' as described below.

Each of the housing plates 107 and 107' of the present invention is equipped to hold one guide plate 113 and 113' respectively. In an embodiment, the crimper 100 includes two guide plates viz. 113 and, 113' referred to as "right guide plate" and "left guide plate". In an embodiment, both the guide plates 113/113' are mirror images of each other i.e. the guide plate 113' is a mirror image of the guide plate 113. The guide plates 113, 113' form a housing when they are fixed to each other. The jaws 111 and gear pins 117 are housed within the housing formed by assembling the guide plates 113, 113'.

Figure 7:
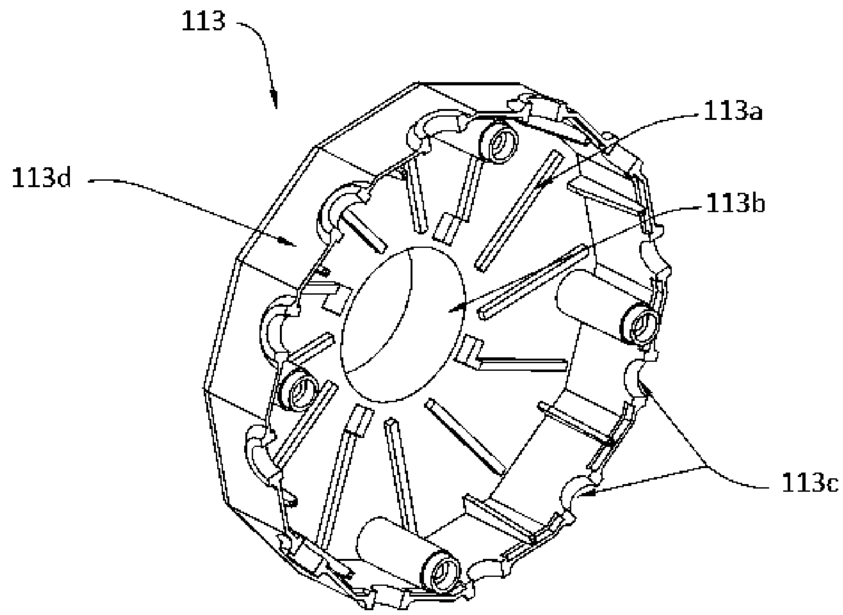
FIG. 7 illustrates a guide plate 113 of the crimper 100 in accordance with an embodiment of the present disclosure.

FIG. 7 shows a single guide plate 113 of a preferred embodiment. The other guide plate 113', being the mirror image of guide plate 113, is not shown. As shown in FIG. 7, the guide plate 113 includes an outer periphery having a pre-defined shape such as a polygonal shape shown in FIG. 7. In an embodiment, the number of sides of the polygon is same as the number of jaws 111. Each guide plate 113/113' may include a raised guide edge 113*d* with an outer periphery as shown in FIG. 7 to give it a tray-like shape.

The raised guide edge 113*d* may include an outer periphery having a polygonal shape with an outer dimension smaller than an internal diameter of the gear rings 115. The number of sides of the polygon is same as the number of jaws 111 and gear pins 117. Alternately, the raised guide edge 113*d* may include an outer periphery having a circular round shape with an outer diameter smaller than the internal diameter of the gear rings 115.

The outer periphery of the guide plate 113/113' has an outer dimension which is smaller than the internal diameter of the gear rings 115 (described below) such that the guide plates 113/113' can be accommodated within the gear rings 115. Each guide plate 113/113' is concentrically fitted inside the corresponding housing plate 107/107' within the inner circumference of the gear ring 115 such that the housing plate is free to rotate relative to the corresponding guide plate 113/113'.

The guide plates 113/113' may include a plurality of linear guides 113*a*. Each of the linear guides 113*a* may be same or different from each other. In an embodiment, the linear guides 113*a* are identical. As shown in FIG. 7, the linear guides 113*a* extend from a central portion of the guide plate 113 in a radial direction away from the central portion. The other guide plate 113' also has similar linear guides 113*a*' corresponding to mirror images of the linear guides 113*a* of guide plate 113. The linear guides 113*a*/113*a*' in guide plates 113/113' may be in the form of rails which guide the movement of jaws 111. In an embodiment, the number of linear guides 113*a*/113*a*' is equal to the number of jaws 111. In an embodiment, the number of linear guides 113/113' and the number of jaws 111 is twelve.

Each linear guide 113*a*/113*a*' includes a pre-defined width and a pre-defined length. Each linear guide 113*a* fits in one of the grooves 111*b* of one of the jaws 111. As described above, each jaw 111 has two grooves 111*b* and 111*b*' one on each side. The other groove 111*b*' of the same jaw 111 engages with a corresponding linear guide 113*a*' in the other guide plate 113'. This arrangement helps the jaws 111 to move by sliding over these linear guides 113*a*/113*a*' in the radial direction. Hence, the direction of the radial movement of the jaws 111 is controlled by the linear guides 113*a*/113*a*'.

The guide plate 113/113' may include a guide opening 113*b* at its center (or central guide opening 113*b*) and a number of partial openings 113*c* on the raised guide edge 113*d*. In an embodiment, the number of partial openings 113*c* is equal to the number of jaws 111. In an embodiment, the guide opening 113*b* is circular. Similarly, the partial openings may be roughly semi-circular.

As shown in FIG. 7, the exemplary guide plate 113 includes twelve linear guides 113*a* for guiding the movement of corresponding twelve jaws 111. It has also twelve partial openings 113*c*. The other guide plate 113' includes same number of linear guides 113*a*' and partial openings 113*c*. A skilled person will understand that number of jaws 111 and the linear guides 113*a*/113*a*' may be less than or more than twelve.

Figure 8:
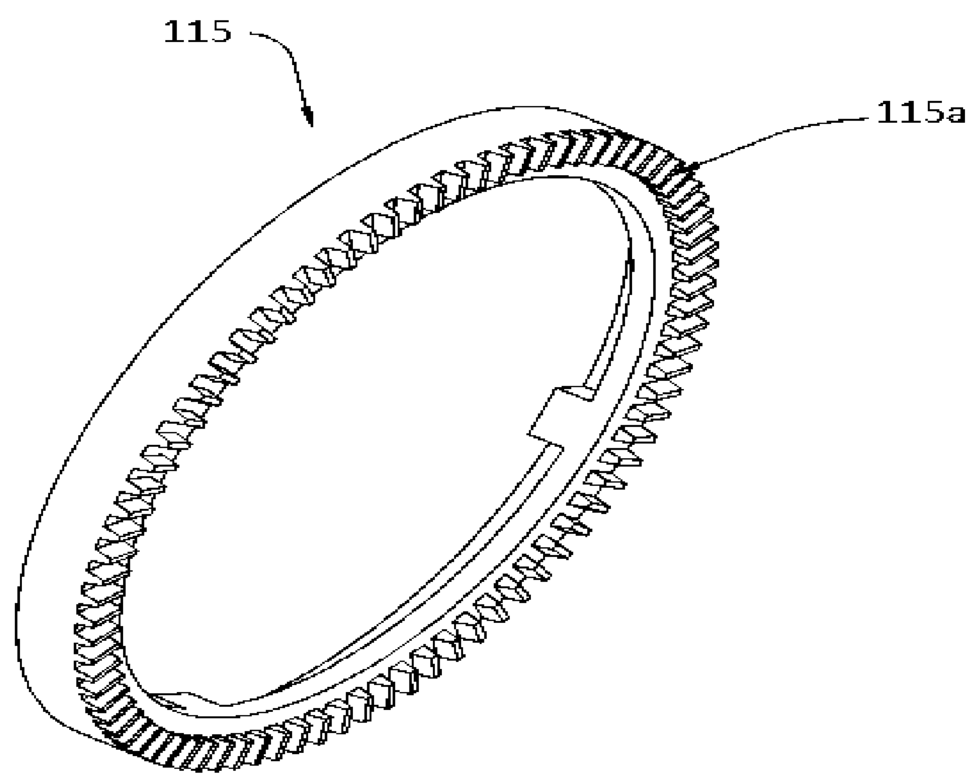
FIG. 8 depicts a gear ring 115 of the crimper 100 in accordance with an embodiment of the present disclosure.

The at least one of the housing plates 107/107' is provided with a gear ring 115 which is concentrically fixed inside the housing plate 107/107'. In an embodiment, the crimper 100 includes a single gear ring 115. In an alternate embodiment, the crimper 100 includes two gear rings 115, e.g., a "right gear ring" and "left gear ring". As shown in FIG. 8, the gear ring 115 has a circular (round) shape and has threads 115*a* on its side. In case of two gear rings, both the gear rings 115 may be identical. Owing to similarity in structure, both the gear rings are interchangeably referred by reference numeral '115'. Each of the gear rings 115 includes an internal diameter (inner diameter) which defines an inner circumference of the gear rings 115 and an outer diameter which defines an outer circumference of the gear rings 115. In an embodiment, the outer diameter of the gear ring 115 is smaller than the internal diameter of the circular raised edge e1 of the housing plates 107/107' so that each gear ring 115 can be fixed inside the housing plate 107/107' within the circular raised edge e1 of respective housing plate 107/107' (right or left). The internal diameter of the gear ring 115 is larger than the outer dimension of the guide plate 113 so that the guide plate 113 can be placed within the internal periphery of the gear ring 115. The threads 115*a* of the gear ring 115 mate with the threads on a head portion 117*a* of the gear pin 117 described below.

The crimper includes a plurality of gear pins. Each of the gear pins 117 may be same or different. In an embodiment, the gear pins 117 are identical to each other. The number of gear pins 117 may be equal to the number of jaws 111. Owing to the presence of twelve jaws 111 and twelve linear guides 113*a*/113*a*' in a preferred embodiment of the present invention, the crimper 100 includes twelve gear pins 117. However, depending upon the number of jaws and linear guides, the number of gear pins may be more or less than twelve.

Figure 9:
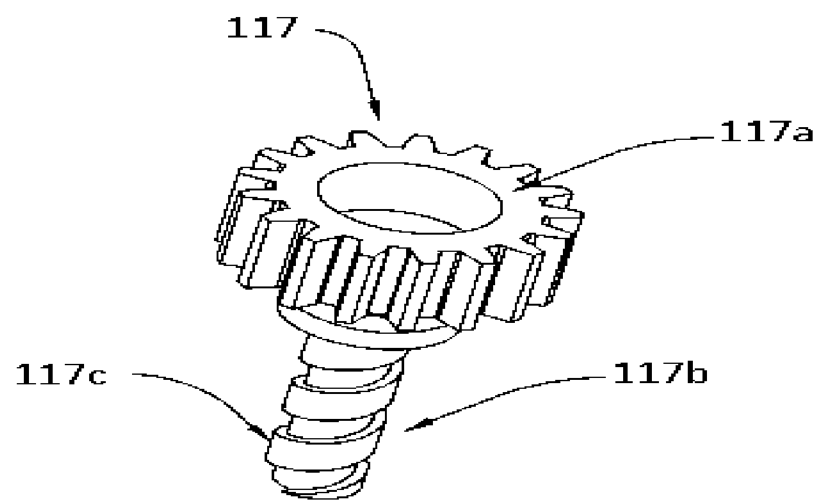
FIG. 9 depicts a gear pin 117 of the crimper 100 in accordance with an embodiment of the present disclosure.

FIG. 9 shows an exemplary embodiment of the gear pin 117. Each of the gear pin 117 includes an upper round head (or a head portion) 117*a* and a lower pin portion (or pin portion) 117*b*. The diameter of the head portion 117*a* is larger than diameter of the pin portion 117*b*. The upper round head 117*a* includes external threads that mate with the threads 115*a* present in the gear rings 115. The lower pin portion 117*b* also includes threads 117*c* that mate with the threads in the hole 111*c* of the jaws 111 (described above).

The above stated external as well as internal components are assembled to form the crimper 100 of the present invention.

Figure 10:
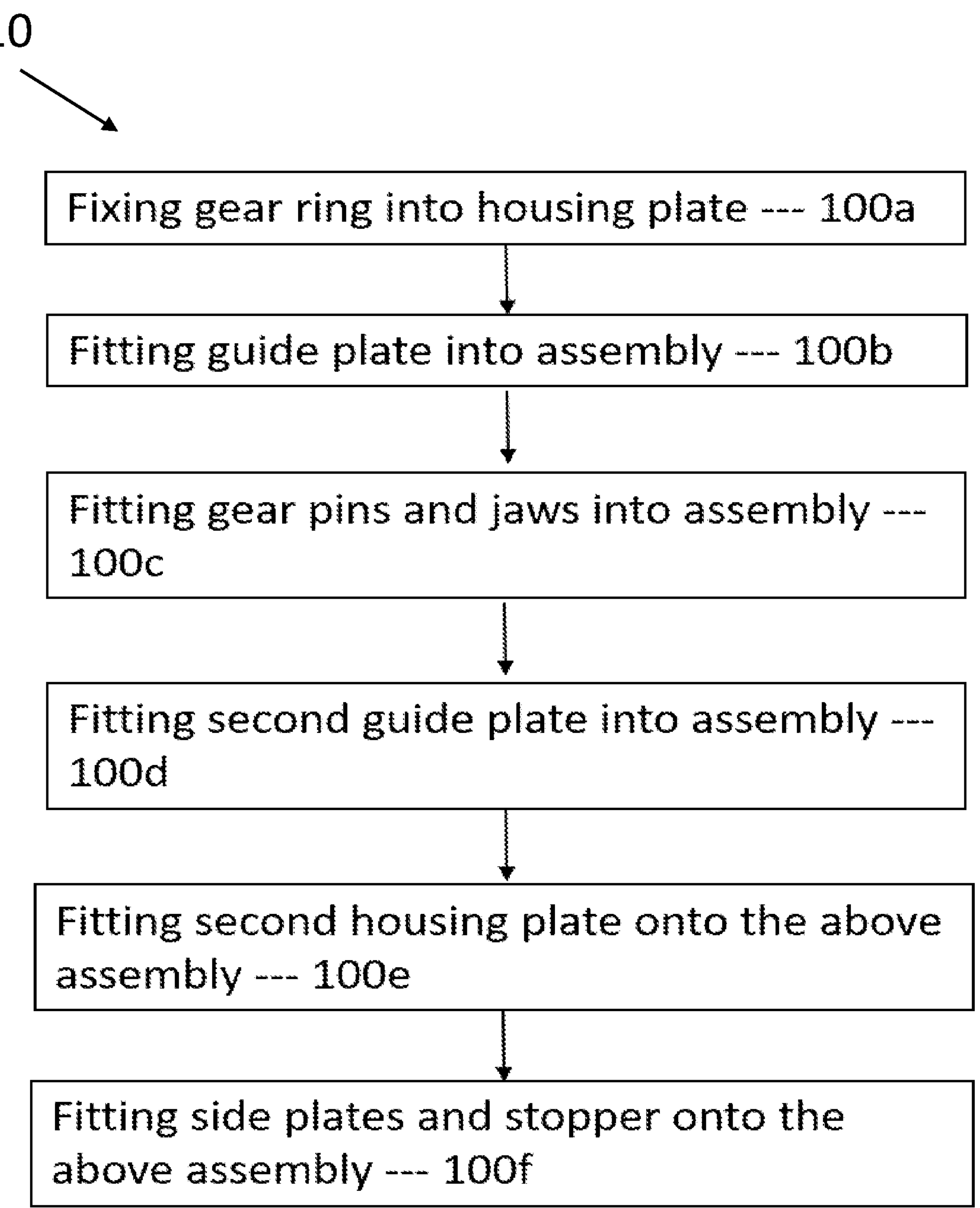
FIG. 10 shows a flowchart of method for assembling the crimper 100 in accordance with an embodiment of the present disclosure.

The method of assembly of the foregoing crimper 100 is depicted in FIG. 10.

Figure 10A:
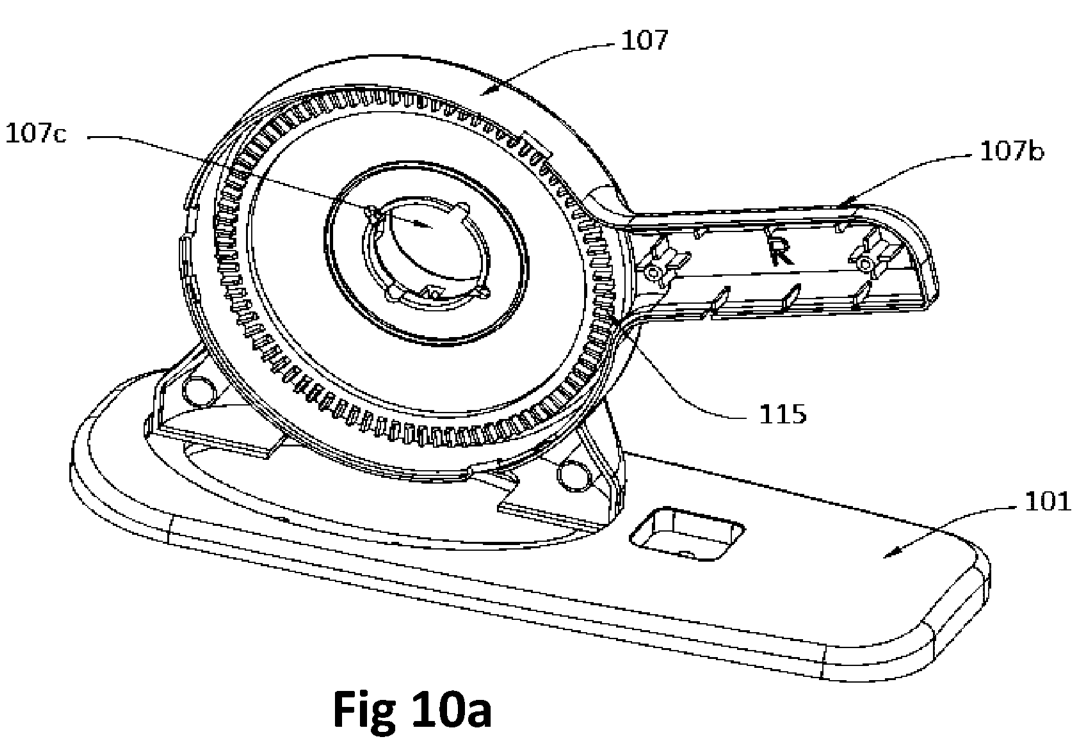
FIG. 10*a*-10*i* depicts the different stages in assembly of the crimper 100 in accordance with an embodiment of the present disclosure.

The method 10 commences at step 100*a* where one of the at least one gear ring 115 is fixed concentrically into one of the housing plate 107. In case of the presence of another guide ring 115, the remaining gear ring 115 may be fixed into the other housing plate 107'. The embodiment of the assembly of the right housing plate 107 and the gear ring 115 is depicted in FIG. 10*a* where the housing plate 107 is shown as placed on the base plate 101. However, it is not necessary that the assembly is made on the base plate 101.

In an embodiment, in case of two gear rings 115, one of the gear rings 115 is so fitted that it is free to rotate relative to the housing plate 107 in which it is fitted, while the other gear ring 115 is fixed firmly in the housing plate 107' so that it is not free to rotate relative to the housing plate 107' in which it is fitted. Alternately, both the gear rings 115 may be firmly fixed into the respective housing plates 107 and 107' such that none of them are free to rotate relative to the respective housing plates 107/107' in which they are fitted. In another embodiment, one of the housing plates e.g. 107 is provided with a gear ring e.g. 115 which is firmly fixed in the housing plate 107, while the other housing plate 107' is not provided with a gear ring 115. In the preferred embodiment, one of the gear rings 115 is free to rotate while the other is fixed firmly and is not free to rotate.

Figure 10B:
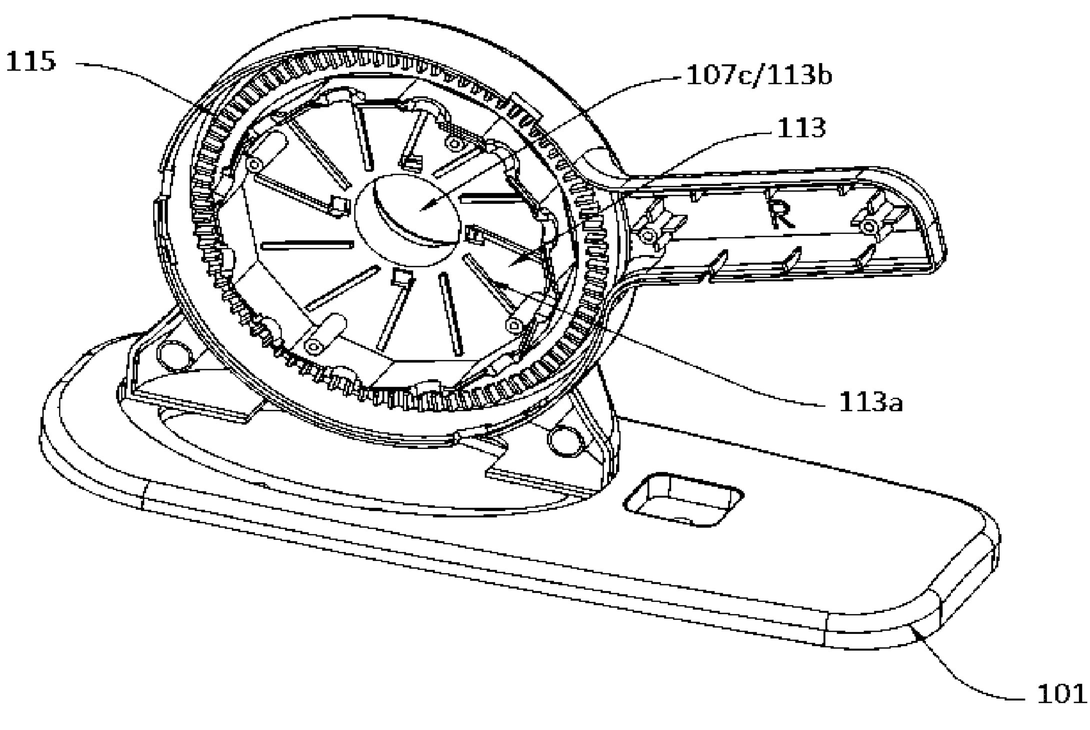

At step 100*b*, one of the guide plates 113 is concentrically placed and fitted into the assembly of housing plate 107 and gear ring 115 of FIG. 10*a*. As the outer dimension of the guide plate 113/113' is less than the inner diameter of the gear ring 115, the guide plate 113/113' can be placed within the inner circumference of the gear ring 115. The guide plate 113 is placed concentrically within the inner circumference of the gear ring 115 fitted inside the housing plates 107 such that central housing opening 107*c* of the housing plate 107 is concentric with the central guide opening 113*b* of the guide plate 113/113'. FIG. 10*b* shows an assembly with the guide plate 113 fitted in this manner. As shown in FIG. 10*b*, the guide plate 113 fits within the inner circumference of the gear ring 115 fitted into the housing plate 107. In this embodiment, the guide plate 113 is fitted such that the housing plate 107 can freely rotate relative to the guide plate 113. Note that the linear guides 113*a* extend in the radial direction.

Figures 10C, 10D:
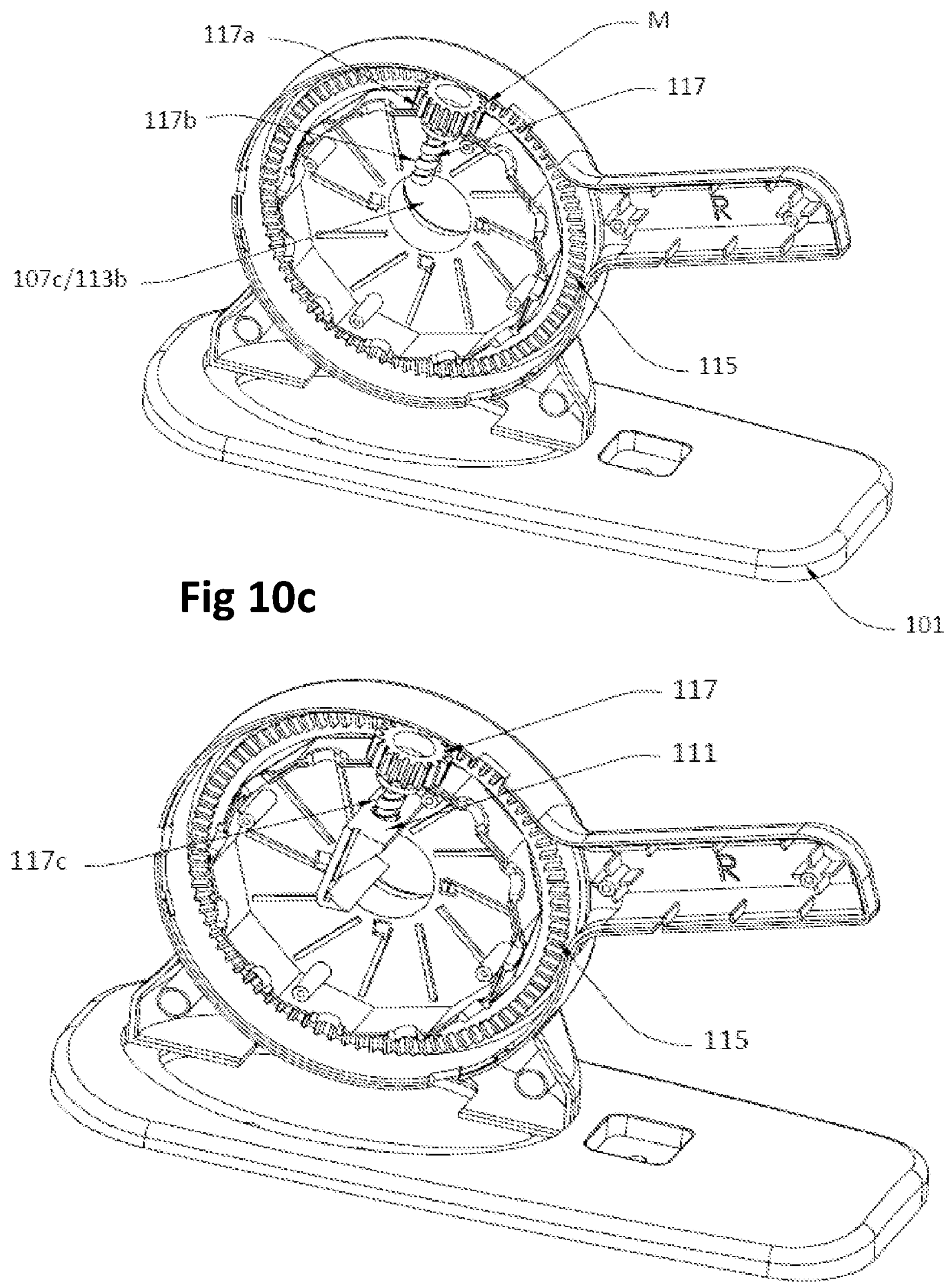

At step 100*c*, the gear pins 117 and the jaws 111 are then fixed/fitted into the above assembly. To make this arrangement clear, the above assembly is shown in FIG. 10*c* with one gear pin 117 (without the jaw 111) in one of the assemblies. As shown in FIG. 10*c*, the head portion 117*a* of the gear pin 117 projects out from the guide plate 113 through a partial opening 113*c* and the pin portion 117*b* projects inside the guide plate 113. This allows the external threads on the head portion 117*a* of the gear pin 117 to engage with the threads 115*a* of the gear ring 115 at M (threaded engagement). In addition, the pin portion 117*b* of the gear pin 117 rests in the partial opening 113*c* on the raised guide edge 113*d* of the guide plate 113 such that all the gear pins 117 are free to rotate on their respective axis. It may be noted that the gear pin 117 as shown does not have support and it cannot remain in this position as shown. The assembly should be laid flat. FIG. 10*c* is provided just to illustrate how the gear pin 117 will ultimately be fixed.

In order to fix the jaws 111 to the gear pins 117, the threads 117*c* on the pin portion 117*b* of the gear pin 117 are engaged with the threads in the hole 111*c* in the jaw 111 (threaded connection). FIG. 10*d* shows a view of a single gear pin 117 along with one jaw 111. Care is taken while fitting the jaws 111 such that one of the grooves e.g. 111*b* of the jaw 111 aligns with one of the linear guides 113*a* of the guide plate 113 and engages with one of the linear guides 113*a* of the guide plate 113. It may be noted that the gear pin 117 and the jaw 111 as shown do not have support and they cannot remain in this position as shown. The assembly should be laid flat. FIG. 10*d* is provided just to explain how the gear pin 117 and the jaw 111 will ultimately be fixed.

Figure 10E:
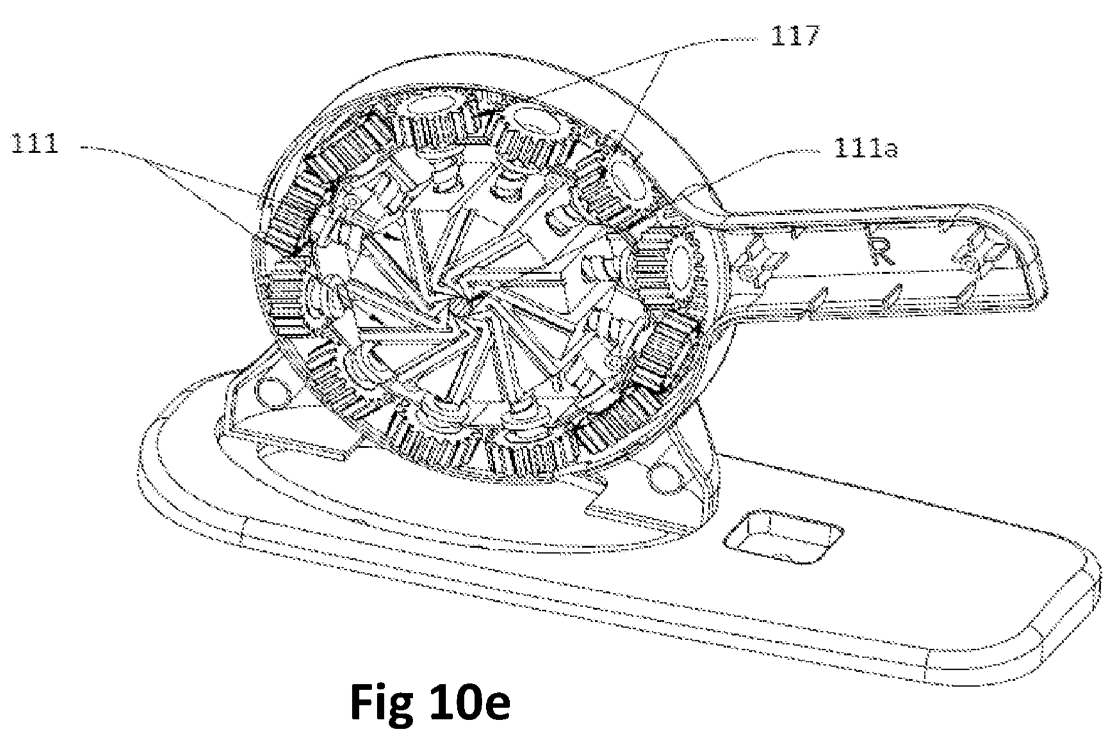

All the gear pins 117 and all the jaws 111 are similarly assembled inside the guide plate 113 as shown in FIG. 10*e*. All the jaws 111 are arranged such that each jaw 111 engages same number of threads of the gear pin 117 with which it is engaged so that all the jaws 111 are at the same radial distance from the center of the guide plate 113. Thus, all the jaws and the gear pins are fixed in a manner that the tapered portions of all jaws collectively form a uniform polygonal iris opening. Further, as the tapered surface 111*d* of one jaw 111 is in contact with the corresponding tapered surface 111*d* of the adjacently placed jaw 111, the above assembly remains stable preferably when placed flat. In addition, the tapered surfaces 111*d* of all jaws 111 when placed together in this manner, i.e. when all the jaws 111 are at the same radial distance from the centre of the guide plate 113, form the iris opening 111*a* at the center as evident in FIG. 10*e*.

Figure 10F:
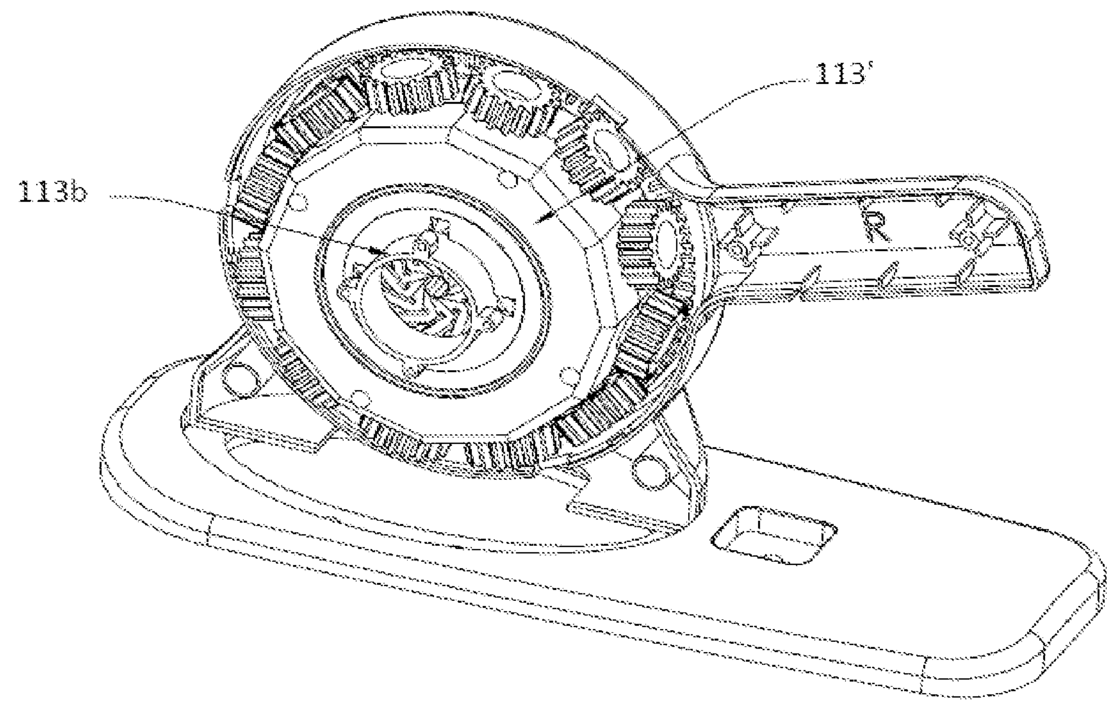

At step 100*d*, the second guide plate 113' is concentrically and firmly placed and fixed/fitted onto the first guide plate 113 in the above assembly as shown in FIG. 10*f*. The central guide opening 113*b* of the second guide plate 113' is concentric with the central guide openings 113*b* of the first guide plate 113 and central housing opening 107*c* of the first housing plate 107. The guide plates 113 and 113' together form the housing that houses the jaws 111 along with the gear pins 117. Care is taken while fitting the second guide plate 113' such that the linear guides 113*a* of the second guide plate 113' are engaged in the second set of grooves e.g. 111*b*' of the corresponding jaws 111.

As mentioned previously, the head portions 117*a* of the gear pins 117 project out from the assembly of two guide plates 113/113' through partial openings 113*c* of each guide plate 113/113'. The partial openings 113*c* on each of the guide plates 113, 113' now form a full opening through which the upper part of the pin portions 117*b* of all the gear pins 117 projects out from the assembly of two guide plates 113 and 113' such that all the gear pins 117 are free to rotate along their respective axes within these full openings. The housing plate 107 is free to rotate with respect to the guide plates 113/113' in the assembly thus formed.

Figure 10G:
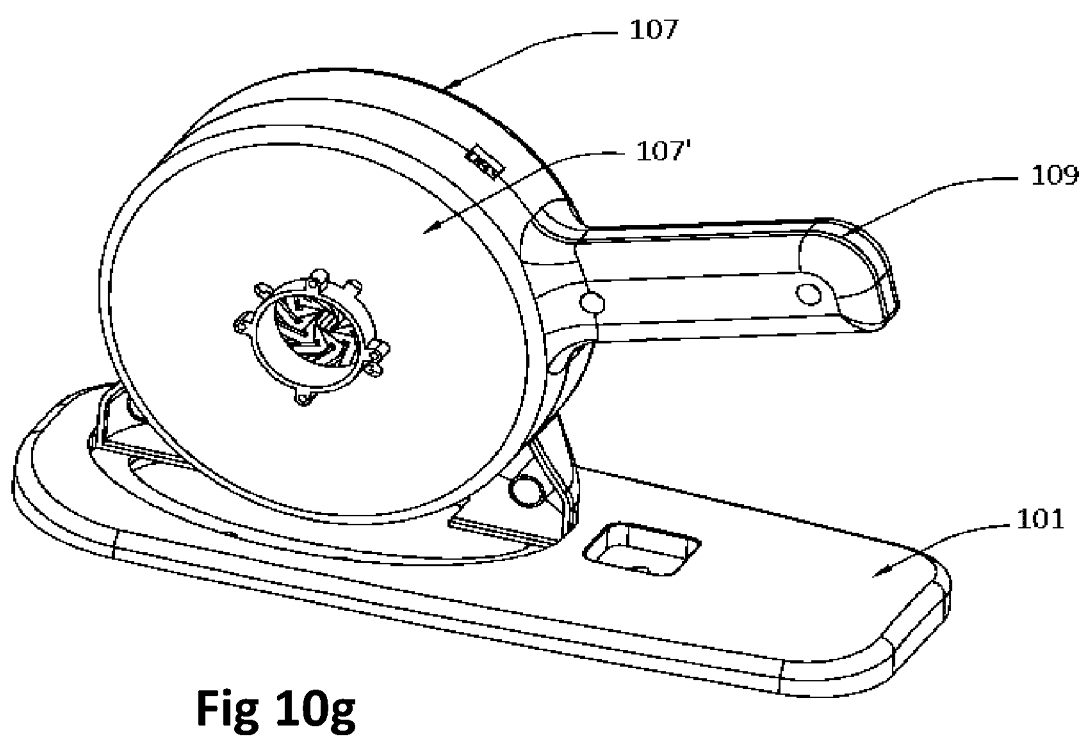

At step 100*e*, the second housing plate 107' (other housing plate 107') is concentrically placed and fitted onto the above assembly to align with the first housing plate 107 as shown in FIG. 10*g* such that the central housing openings 107*c* (of both housing plates 107) and guide openings 113*b* (of both guide plates 113/113') are concentric. Care is taken while fitting the second housing plate 107' such that the threads of the other gear ring 115 (if provided) in the second housing plate 107' are engaged with the threads on the head portion 117*a* of the gear pins 117 and the second housing plate 107' is able to freely rotate relative to the assembly of the guide plates 113 and 113'. The housing plates 107 and 107' are firmly fixed with each other to form the housing 107A such that after fixing, the handle portions 107*b* of the two housing plates 107 and 107' form a complete handle 109 and the housing 107A can rotate freely relative to the assembly of the two guide plates 113 and 113'.

Figure 10H:
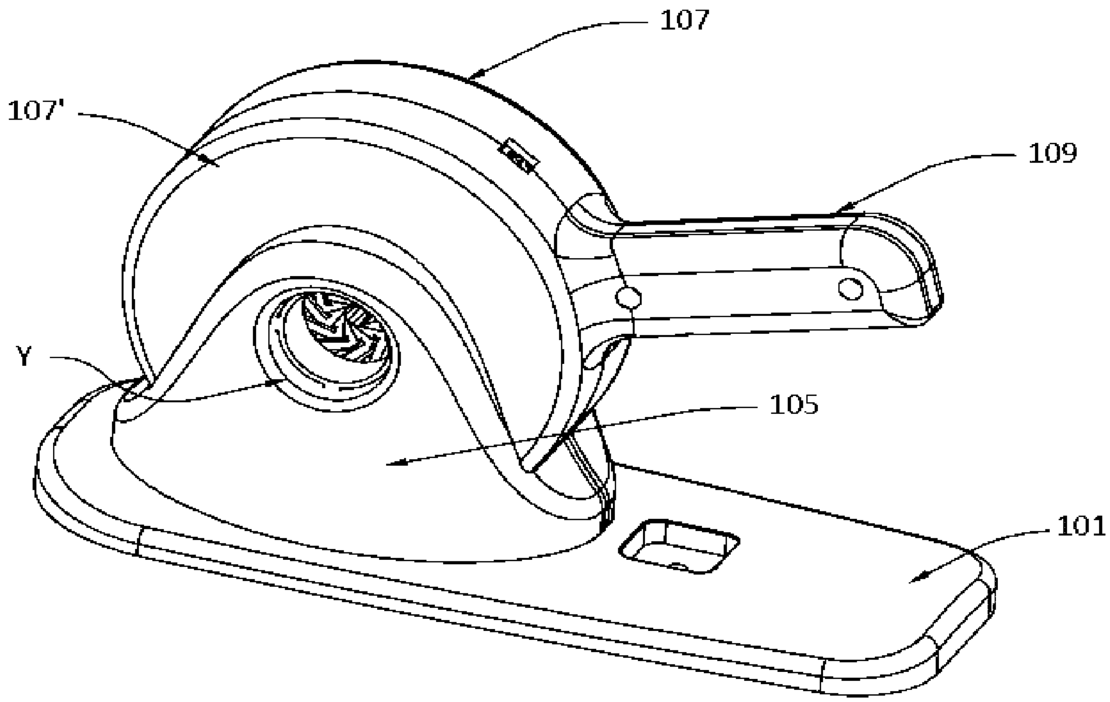

At step 100*f*, the side plates 105 and 105' are fitted onto the above assembly as shown in FIG. 10*h* on each of the sides of the assembly of housing plates 107/107' forming the housing 107A and the guide plates with all internal components. The central openings 105*a* in the side plates 105/105' are concentric with the central housing openings 107*c* of the housing plates 107/107' and the guide openings 113*b* in the guide plates 113/113'; together this arrangement forms a "central round opening" Y shown in FIG. 10*h*. In an embodiment, the side plates 105/105' are firmly fixed with each other such that the housing 107A is free to rotate relative to the side plates 105/105' and the guide plates 113/113' around the central round opening Y. The said assembly of the side plates 105/105', the housing plates 107/107' and the guide plates 113/113', is fixed onto the base plate 101 making the assembly of the side plates 105/105' and the guide plates 113/113' stationary while the housing 107A is free to rotate around the central round opening Y by moving the handle upwards or downwards.

Hence, the central housing opening 107*c* of the housing plates 107/107' and the guide opening 113*b* of the guide plates 113/113' coincide with each other to receive a radially expandable and collapsible prosthetic device within the iris opening 111*a*.

Figure 10I:
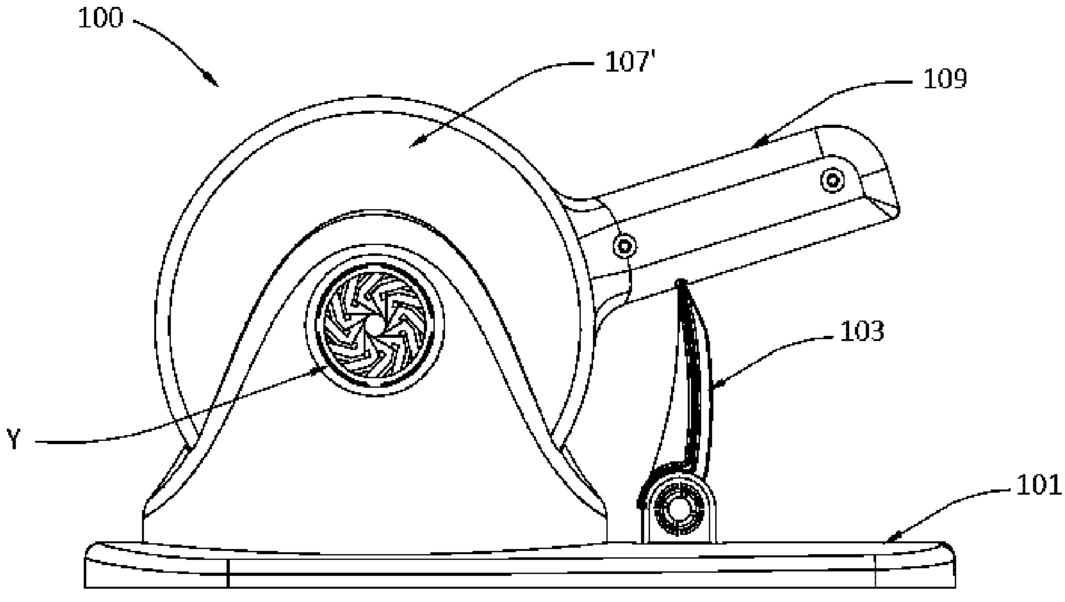

The above assembly is then fitted with the optional removable stopper 103 as shown in FIG. 10*i*. FIG. 10*i* shows the crimper 100 with the stopper 103 set at vertical position where the movement of the handle 109 of the housing plate 107 is restricted by the stopper 103. The handle 109 cannot move further down which restricts the minimum size/diameter of the aperture 111*a* corresponding to the lowest position of the handle 109 as restricted by the stopper 103. When the handle 109 is moved up, the size/diameter of the aperture 111*a* increases and in the uppermost position, this diameter is maximum. If the stopper 103 is shortened, the minimum size/diameter of the aperture 111*a* will reduce. If the stopper 103 is absent, the handle 109 has no restriction in moving further down and size/diameter of the aperture 111*a* can reduce to a very low value.

The above disclosed crimper 100 may operate in a predefined manner as elucidated below. The movement of the handle 109 imparts rotational movement to the housing 107A around the central round opening Y and the internal components placed within the housing formed by the two guide plates 113 and 113'. This movement results in rotation of the gear rings 115 which in turn rotates the head portions 117*a* of the gear pins 117. The pin portions 117*b* of the gear pins 117 also rotate within the internal threads of the hole 111*c* at the top surface 111*e* of the respective jaws 111 thereby causing the jaws 111 to move linearly by sliding along the linear guides 113*a*/113*a'* of the guide plates 113/113' in radial direction in a synchronized manner. This movement of the jaws 111 changes (reduces or increases) the size of the aperture (iris opening) 111*a* formed by the tapered surfaces 111*d* of the jaws 111. When the handle 109 is moved in upward direction, the gear ring(s) 115 rotate in the same direction. This motion rotates the gear pins 117 such that jaws 111 move away from each other increasing the size/diameter of the iris opening 111*a*. Moving the handle 109 in downward direction would, similarly cause the jaws 111 to move closer to each other reducing the size/diameter of the iris opening 111*a*.

The method of crimping using the crimper 100 of the present invention involves placing the crimped medical device (in at least partially expanded condition) onto the deflated balloon of the delivery system. If desired, the balloon may be partially inflated so that the medical device can be fitted better onto the balloon. The handle 109 of the crimper 100 is then moved in an upward direction to increase the size of the iris opening 111*a* more than the diameter of the prosthetic device which may be in at least a partially expanded condition. The balloon and the prosthetic device are at least partially introduced/placed across the iris opening 111*a* of the crimper 100. The handle 109 is then gradually moved in the downward direction to reduce the size of the iris opening 111*a* causing reduction in the diameter of the prosthetic device i.e. crimping of the prosthetic device. This downward movement is controlled manually so as to achieve reduction in the size of the iris opening 111*a* in a gradual manner. Alternately, this downward movement may be automated. The downward movement of the handle 109 is stopped when desired crimping is achieved which may be in more than one stages. The crimped diameter of the prosthetic device may either be controlled by stopping downward movement of the handle 109 by judgment or by restricting further downward movement of the handle 109 by the stopper 103.

At this stage, the handle 109 is moved upwards to increase the size of the iris opening 111*a* and the prosthetic device crimped on the balloon is removed from the aperture 111*a* of the crimper 100.

Subsequently, the crimped prosthetic device is checked whether desired level of crimping is achieved. If further crimping is required to reduce the crimped diameter further, the crimping operation is repeated and the handle 109 is further moved down compared to the previous position.

The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

We claim:

1. A crimping device for crimping a radially expandable and collapsible prosthetic device for reducing its diameter from at least a partially expanded state to a crimped state, the crimping device comprising:

a base plate;

two housing plates fixed over the base plate such that the housing plates are free to rotate relative to the base plate, each housing plate having a circular tray portion with a central housing opening and a handle portion extending from the tray portion, wherein when the two housing plates are assembled, the tray portions of each of the two housing plates form a first housing for accommodating other components of the crimping device while the handle portions of each of the two housing plates form a handle, at least one of the housing plates is provided with a circular gear ring which is concentrically fixed inside the housing plate, the gear ring being provided with threads, the gear ring having an inner diameter defining an inner circumference and an outer diameter defining an outer circumference;

two guide plates fixed to each other forming a second housing, each guide plate concentrically fitted inside the corresponding housing plate within the inner circumference of the gear ring such that the housing plate is free to rotate relative to the corresponding guide plate, each guide plate having a central guide opening, and a plurality of identical linear guides in the form of rails extending from a central portion of the guide plate extending in a radial direction away from the central portion, each linear guide having a width and a length;

a plurality of identical jaws, each of the jaws having a top surface, a tapered surface and two sides, each jaw further including:

a hole in the top surface, the hole having internal threads, two grooves, one on each of the two sides of the jaws, wherein width of said grooves corresponds to the width of the linear guides of guide plates such that a linear guide fits inside a groove and a jaw can slide smoothly over the linear guide, and wherein the tapered surface of each of the jaws collectively form an iris opening when all the jaws are assembled, wherein a size of the iris opening can be varied by controlled movement of the jaws in a synchronous manner on movement of the handle; and a plurality of identical gear pins, each gear pin including a head portion and a threaded pin portion, wherein the head portion having external threads that mate with the threads of the gear ring and the threads on the pin portion mate with the threads in the holes in the top surface of the jaw, wherein the central housing opening of the housing plates and the central guide opening of the guide plates coincide with each other to receive a radially expandable and collapsible prosthetic device within the iris opening formed by the jaws for crimping the prosthetic device, wherein movement of the handle imparts rotational motion to the housing plates around a central round opening, which rotates the gear ring which in turn rotates the head portions of the gear pins, thereby causing the threads in the pin portion of the gear pins to rotate within the internal threads of the holes at the top of the jaws causing the jaws to move in radial direction guided by the linear guides in the guide plates causing the size of the iris opening to change.

2. The crimping device of claim 1 wherein, the housing plates are held between two side plates that are fixed on the base plate such that the housing plates are free to rotate relative to the side plates.

3. The crimping device of claim 1 wherein, each housing plate has an internal diameter and a raised edge.

4. The crimping device of claim 3 wherein the gear ring has an outer diameter which is smaller than an internal diameter of the raised edge of the housing plates.

5. The crimping device of claim 1 wherein the head portion of each gear pin includes a diameter which is larger than a diameter of the pin portion of the gear pin.

6. The crimping device of claim 1 wherein, the guide plates include a raised guide edge having a circular round shape outer periphery with an outer diameter smaller than an internal diameter of the gear ring.

7. The crimping device of claim 1 wherein, the guide plates include a raised guide edge having a polygonal shape outer periphery with an outer dimension smaller than an internal diameter of the gear ring.

8. The crimping device of claim 7 wherein, a number of sides of the polygon is same as the number of jaws.

9. The crimping device of claim 1 wherein a number of gear pins and the number of linear guides in each guide plate is same as the number of jaws.

10. The crimping device of any of claims 1-9 wherein, the number of linear guides in each guide plate, the number of gear pins and the number of jaws is twelve.

11. The crimping device of claim 1 wherein, the number of linear guides in each guide plate, the number of gear pins and the number of jaws is more or less than twelve.

12. The crimping device of any of claims 1-9 or 11 wherein, the gear ring is firmly fixed into one of the housing plates while the other housing plate does not have a gear ring.

13. The crimping device of any of claims 1-9 or 11 wherein, a gear ring is fixed in each of the housing plates, wherein, one gear ring is free to rotate while the other gear ring is firmly fixed in respective housing plate.

14. The crimping device of claim 1 wherein, a gear ring is fixed in each of the housing plates, wherein, each gear ring is fixed firmly in respective housing plate.

15. The crimping device of any of claims 1-9, 11, or 14 wherein, the gear ring is fixed into one of the housing plates such that the gear ring is free to rotate while the other housing plate does not have a gear ring.

16. The crimping device of any of claims 1-9, 11, or 14 wherein, the crimping device is made from a polymeric material or metallic material or a combination of these materials.

17. The crimping device of any of claims 1-9, 11, or 14 wherein, the base plate includes one or more stoppers which may be removably fixed on the base plate to restrict the downward movement of the handle defining a lowermost position of the handle to prevent the size of the iris opening from reducing further.

18. The crimping device of any of claims 1-9, 11, or 14 wherein, the prosthetic device is one of a balloon expandable prosthetic device or a self-expandable prosthetic device.

19. The crimping device of any of claims 1-9, 11, or 14 wherein, the prosthetic device is one of a vascular stent or a trans-catheter prosthetic heart valve.

20. A method of assembling a crimping device, the method comprising of:

fixing one gear ring inside at least one of two housing plates, placing a guide plate concentrically within an inner circumference of the gear ring such that the at least one of the two housing plate is capable of rotating freely relative to the guide plate, fixing a plurality of gear pins on each guide plate such that a head portion of each gear pin is threadedly engaged with the gear ring, wherein, post engagement, each gear pin is free to rotate on its respective axes, aligning a groove of a plurality of grooves of a plurality of jaws with respective linear guides of the guide plate and simultaneously fixing the plurality of jaws to respective pin portions of the gear pins by providing a threaded connection between a pin portion and the jaw, the fixing of the plurality of jaws resulting in a uniform polygonal iris opening, wherein, all the jaws engage same number of threads of the pin portions so that all the jaws are at the same radial distance from the center of the guide plate, placing a second guide plate concentrically and firmly fixed onto the guide plate forming a second housing that houses the gear pins and the jaws attached to each other, placing the other housing plate onto the second guide plate concentrically such that the other housing plate can freely rotate relative to the assembly of the guide plates, fixing both of the two housing plates firmly with each other such that a first housing is formed after fixing including a handle formed by handle portions of the two housing plates.

21. The method of assembling the crimping device as claimed in claim 20 wherein, the fixing includes fixing one gear ring inside one of the two housing plates such that the gear ring is either free to rotate or fixed firmly.

22. The method of assembling the crimping device as claimed in claim 20 wherein, the fixing a plurality of gear pins includes engaging a head portion of each gear pin that projects out from the guide plate, including external threads with threads of the gear ring fixed inside the at least one of the two housing plates.

23. The method of assembling the crimping device as claimed in claim 20 wherein, the fixing the plurality of jaws to the respective gear pins includes threading a pin portion of each gear pin in internal threads of a hole provided on a top surface of the jaw.

24. The method of assembling the crimping device as claimed in claim 20 wherein, aligning a plurality of jaws includes engaging one of the plurality of grooves on a side of each jaw with one of the linear guides of the guide plate.

25. The method of assembling the crimping device as claimed in claim 20 wherein, the fixing of the plurality of jaws resulting in the uniform polygonal iris opening includes fixing tapered portions of all jaws in the guide plate to form a uniform polygonal iris opening.

26. The method of assembling the crimping device as claimed in claim 20 wherein placing a second guide plate includes engaging a second set of grooves of the corresponding jaw with the linear guides of the second guide plate, and allowing the head portions of the gear pins project out from the assembly of two guide plates such that the gear pins are free to rotate along their respective axes.

27. The method of assembling the crimping device as claimed in claim 20 wherein, placing the other housing plate onto the second guide plate concentrically includes mating the threads on the head portions of all the gear pins with the threads of the gear ring placed inside the other housing plate if provided.

28. The method of assembling the crimping device as claimed in claim 20 wherein, the method of assembling includes fitting one or more side plates on each side of the two housing plates such that the openings in the side plates are concentric with central housing openings of the two housing plates and the guide openings of the guide plates forming a central round opening, thereby the two housing plates being free to rotate relative to the side plates and guide plates around the central opening.

29. The method of assembling the crimping device as claimed in claim 20 wherein, the method of assembling includes fixing assembly of one or more side plates, the two housing plates and the guide plates onto a base plate making the assembly of the one or more side plates and the guide plates stationary and the assembly of housing plates free to rotate around a central round opening by moving the handle upwards or downwards.

30. The method of assembling the crimping device as claimed in claim 20 wherein, fixing the gear ring includes fixing the gear ring firmly into one of the two housing plates.

31. The method of assembling the crimping device as claimed in claim 20 wherein, fixing the gear ring includes fixing one gear ring in a manner that the gear ring is free to rotate in one of the two housing plates.

32. The method of assembling the crimping device as claimed in claim 20 wherein, fixing the gear ring includes fixing one gear ring firmly in respective housing plate while the other gear ring is free to rotate.

33. A method of assembling a crimping device, the method comprising:

fixing one gear ring inside at least one of two housing plates such that the gear ring is either free to rotate or fixed firmly in the respective housing plate, placing a guide plate concentrically inside one of the two housing plates within an inner circumference of the gear ring fitted in the respective housing pate such that the respective housing plate is capable of rotating freely relative to the guide plate, fixing a plurality of gear pins such that a head portion of each gear pin projects out from the guide plate thereby allowing engagement of external threads on the head portion with threads of the gear ring fixed inside the at least one of the two housing plates, wherein all the gear pins are free to rotate on their respective axes, fixing the jaws to the gear pins by threading a pin portion of the gear pin into internal threads of a hole on a top portion of the jaw and a groove of a plurality of grooves on a side of each jaw engages with linear guides of the guide plate, wherein, all the jaws being arranged such that the jaws engage same number of threads of the gear pins so that all the jaws are at the same radial distance from the center of the guide plate, wherein all the jaws and the gear pins being fixed in a manner that the tapered portions of all jaws collectively form a uniform polygonal iris opening, placing a second guide plate concentrically and firmly fixed onto the guide plate forming a second housing that houses the gear pins and the jaws attached to each other such that a second set of grooves of the corresponding jaw gets engaged with the linear guides of the second guide plate, and the head portions of the gear pins project out from the assembly of two guide plates such that the gear pins are free to rotate along their respective axes, placing the other housing plate onto the second guide plate concentrically such that the threads on the head portions of all the gear pins mate with the threads of the gear ring placed inside the other housing plate if provided, such that the other housing plate can freely rotate relative to the assembly of the guide plates, fixing both of the two housing plates firmly with each other such that after fixing, a first housing is formed, handle portions of the two housing plates form a complete handle, and the assembly of both housing plates can rotate freely relative to the assembly of the two guide plates, fitting one or more side plates on each side of the assembly of the housing plates and the guide plates such that a central openings in the one or more side plates are concentric with central housing openings of the housing plates and the guide openings of the guide plates forming a central round opening, fixing the one or more side plates firmly with each other and with the guide plates such that the assembly of the housing plates is free to rotate relative to the one or more side plates and guide plates around the central opening, the above assembly of the one or more side plates, the housing plates and the guide plates is fixed onto a base plate making the assembly of the side plates and the guide plates stationary and the assembly of housing plates is free to rotate around the central round opening, wherein movement of the handle imparts rotational motion to the housing plates around the central round opening, which rotates the gear rings which in turn rotates the head portions of the gear pins, thereby causing the threads in the pin portion of the gear pins to rotate within the internal threads of the holes at the top of the jaws causing the jaws to move in radial direction guided by the linear guides in the guiding plates causing a size of the iris opening to change.

34. A method of crimping a radially collapsible and expandable prosthetic device using the crimping device of claim 1, the method comprising:

moving a handle of the crimping device in an upward direction thereby increasing a size of an iris opening formed by jaws till the size of the iris opening is more than a diameter of the radially collapsible and expandable prosthetic device to be crimped, placing the radially collapsible and expandable prosthetic device in at least partially expanded condition within the iris opening, gradually moving the handle in downward direction thereby reducing the size of the iris opening causing crimping of the prosthetic device in a single step or in multiple steps, controlling the crimped diameter of the prosthetic device either by stopping downward movement of the handle by judgment or by restricting further downward movement of the handle by a stopper, moving the handle in the upward direction to increase the size of the iris opening, removing the crimped prosthetic device from the iris opening.

35. The method of crimping of claim 33, wherein the radially collapsible and expandable prosthetic device is balloon expandable.

36. The method of crimping of claim 33, wherein the step of placing includes placing the radially collapsible and expandable prosthetic device being crimped over a deflated balloon, in the iris opening.

* * * * *